United States Patent [19]

Koehler

[11] Patent Number: 4,812,658
[45] Date of Patent: Mar. 14, 1989

[54] BEAM REDIRECTING

[75] Inventor: Andreas M. Koehler, Somerville, Mass.

[73] Assignee: President and Fellows of Harvard College, Cambridge, Mass.

[21] Appl. No.: 76,868

[22] Filed: Jul. 23, 1987

[51] Int. Cl.$^4$ .............................................. G21K 1/08
[52] U.S. Cl. ...................... 250/396 R; 250/396 ML; 250/398; 250/492.3
[58] Field of Search ................ 250/396 R, 398, 492.3, 250/396 ML; 313/62, 361.1

[56] References Cited

U.S. PATENT DOCUMENTS 3,955,089  5/1976  McIntyre et al. .................... 250/399
4,198,565  4/1980  Ono ..................................... 250/399

FOREIGN PATENT DOCUMENTS 0173926  8/1985  Fed. Rep. of Germany .
0205720  6/1985  Switzerland .

OTHER PUBLICATIONS

Diagram, Classic Gantry.

Primary Examiner—Carolyn E. Fields
Assistant Examiner—John A. Miller

[57] ABSTRACT

A beam is redirected from an initial direction lying along an initial axis to a final direction lying in a plane which intersects the initial axis (the final direction being other than radially away from the axis) by first redirecting the beam from the initial direction to an intermediate direction lying in the plane, and then redirecting the beam within the plane from the intermediate direction to the final direction.

25 Claims, 4 Drawing Sheets

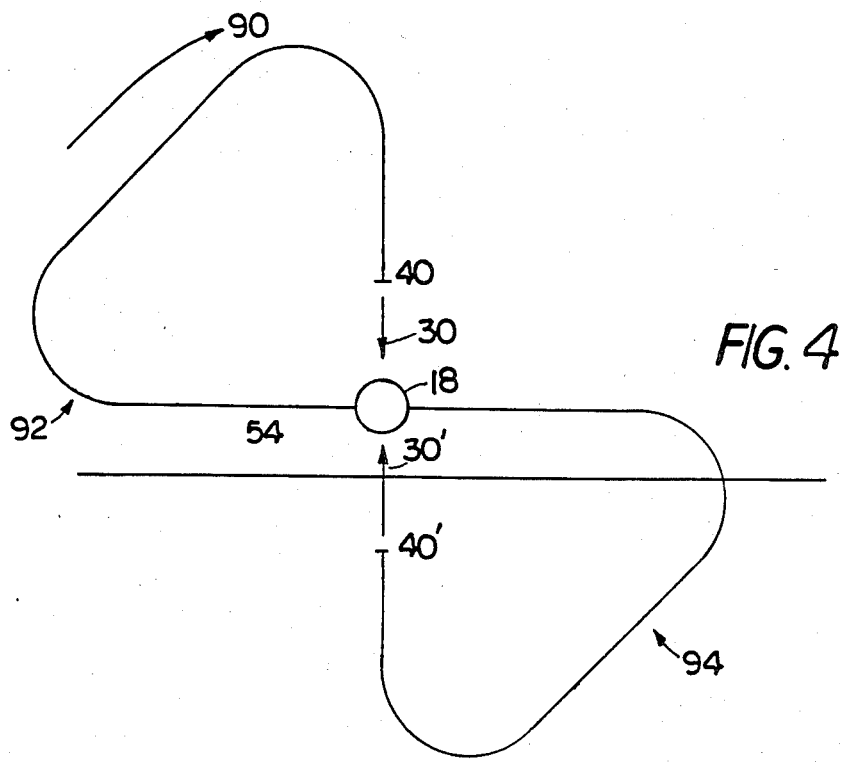
FIG. 4
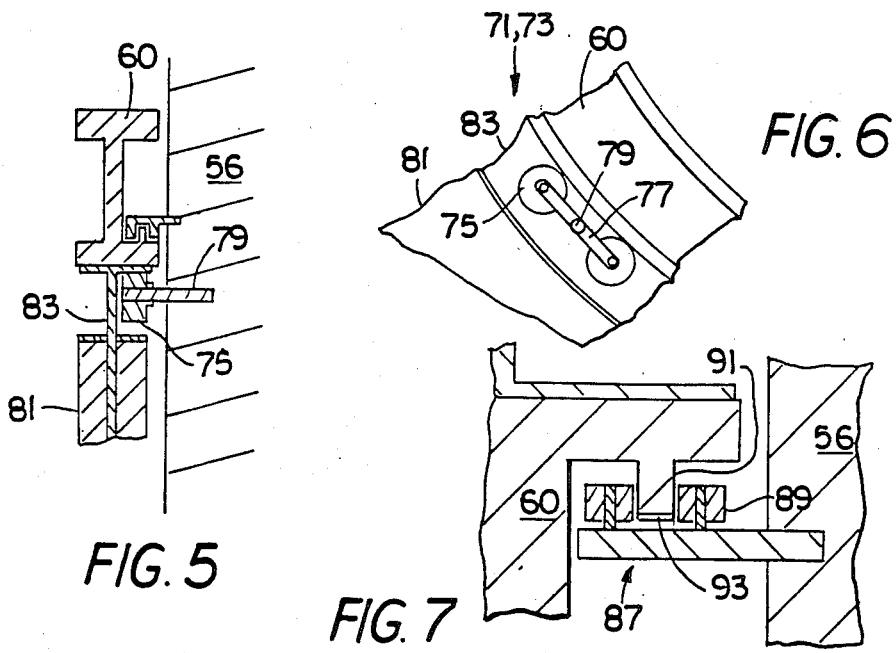
FIG. 5
FIG. 6
FIG. 7

BEAM REDIRECTING

BACKGROUND OF THE INVENTION

This invention relates to redirecting a beam of charged particles.

For medical diagnosis or therapy, it is often desirable to be able to have a beam strike the patient from any one of a range of different directions. In the case of an X-ray beam, the beam source may be compact enough to be moved about a stationary patient to achieve any desired beam direction.

Other kinds of beams (proton beams, for example) are generated by sources (e.g., cyclotrons) that are too massive to be conveniently moved relative to the patient. One way to achieve different beam directions is to move the patient relative to the fixed beam; but moving the patient has disadvantages.

It has also been proposed to hold the patient stationary (e.g., lying down) and provide a movable gantry capable of receiving the beam from the fixed beam source and routing it to the patient along any one of a range of different directions.

In one proposed gantry, the available beam directions all lie in a plane that intersects the tissue to be treated and is perpendicular to the original beam direction from the fixed source. The gantry is U-shaped and swings around an axis defined by the original beam. The original beam is first magnetically redirected typically by 90° to enter one leg of the U and is then bent around the U to the other leg, which lies in the plane of treatment. The beam finally exits that second leg along a path directed toward the tissue. The volume of clear space required to accommodate the swinging gantry is governed by the width and height of the U.

In another proposed gantry system, the beam would first be magnetically redirected 45° and then, after scattering, would be redirected (in the same plane) through an angle of 135° to a path aimed toward the tissue.

SUMMARY OF THE INVENTION

A general feature of the invention is in redirecting a beam from an initial direction lying along an initial axis to a final direction lying in a plane which intersects the initial axis (the final direction being other than radially away from the axis); the beam is first redirected from the initial direction to an intermediate direction lying in the plane, and then is redirected within the plane from the intermediate direction to the final direction.

Preferred embodiments include the following features.

The final direction of the beam may be shifted through a range of orientations. For this purpose, the second redirection structure is mounted for rotation about the axis, and lies generally in a plane. There are a set of distinct counterweights arranged at different positions about the axis for counterbalancing the second redirection structure. The counterweights are configured to provide radiation shielding. Different ones of the counterweights have different weights.

The beam is a proton beam. The plane intersects a region of interest in a body and, in its final direction, the beam is aimed at the region of interest. The plane is perpendicular to the axis. In its final direction, the beam is aimed radially toward the axis.

The first redirection structure redirects the beam segment through an aggregate angle of 90°, by means of two spaced apart substructures that effect respectively two stages (for example each 45°) of redirection of the initial beam. The second redirection structure redirects the beam segment (through an aggregate angle of, for example, approximately 270°) along a pth that lies substantially within a single quadrant of the plane. The second redirection structure includes two spaced apart substructures effecting respectively two stages (for example each 135°) of the redirection of the initial beam. The redirection structures include magnets that form portions of achromats.

The first redirection structure includes a bearing that permits rotation of the first redirection structure about the axis during rotation of the second redirection structure about the axis. The first redirection structure may lie in a plane perpendicular to the treatment plane. While the final direction moves through a 180° range of positions from vertically up to vertically down, the first redirection structure moves through a range of positions that all lie on or above a horizontal plane.

The invention enables a beam from a fixed source to be redirected in any one of a variety of directions, permitting effective diagnosis or treatment, while reducing the volume of space and concrete required to enclose the rotating gantry. A patient may be treated using beam directions that are 180° apart without requiring the floor of the treatment room to accommodate rotation of the segment of the gantry leading to the treatment plane. Counterbalance weights may also effectively provide shielding. The magnets and lens element may be arranged in achromats.

Other advantages and features will become apparent from the following description of the preferred embodiment, and from the claims.

DESCRIPTION OF THE PREFERRED EMBODIMENT

We first briefly describe the drawings.

FIG. 4 is a diagram of a range of locations of the beam path in the treatment plane.

FIG. 5 is a sectional view at 5—5 of FIG. 3.

FIG. 6 is a side view of a supporting wheel assembly.

FIG. 7 is an enlarged sectional view at 7—7 of FIG. 3.

STRUCTURE AND OPERATION

Figure 1:
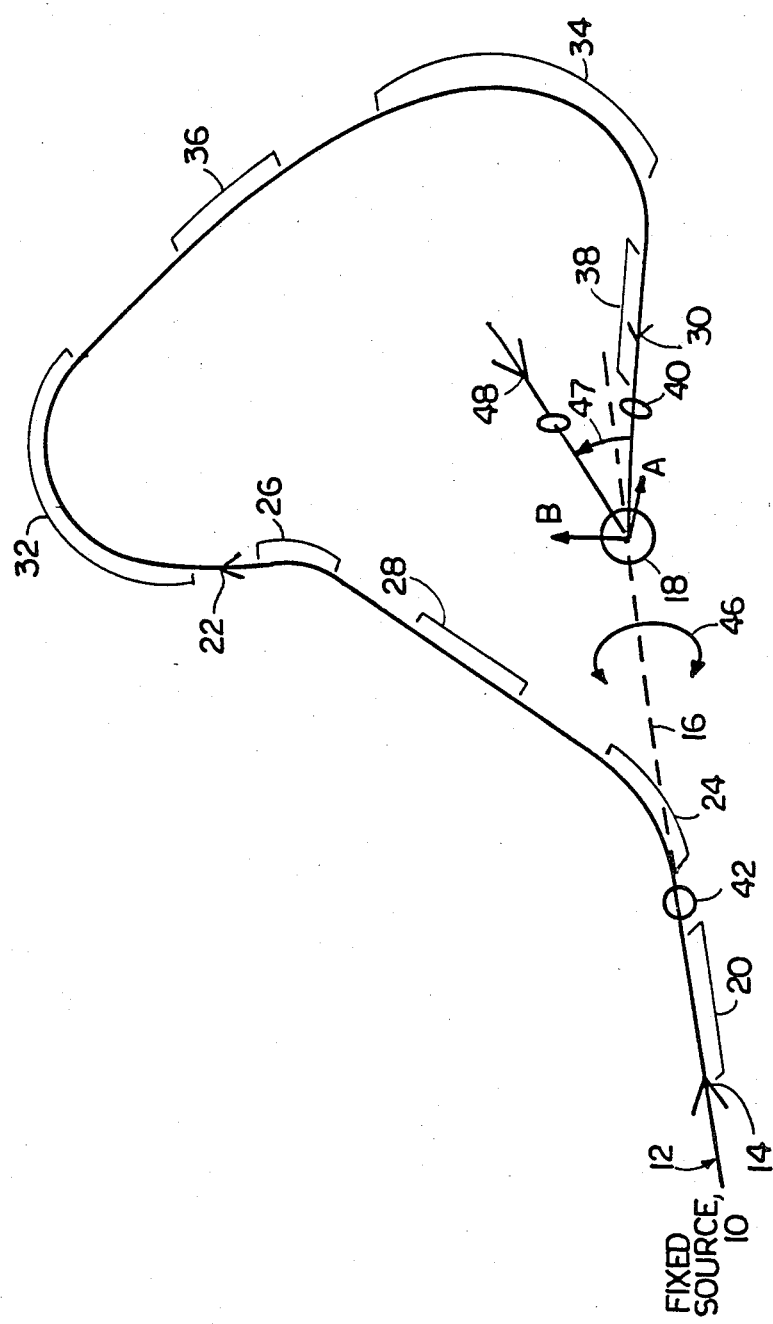
FIG. 1 is a perspective diagram of a path of a beam.

Referring to FIG. 1, a proton beam generated by a fixed source 10 (e.g., a cyclotron) traverses a path 12 that begins in an initial direction 14 along an initial axis 16. Axis 16 intersects an object 18 to be treated (e.g., part of a human body). The beam along path 12 passes through a set of magnetic quadrupole lenses in region 20, and is redirected 90° to an intermediate direction 22 which lies within a plane of treatment (represented by coordinates A, B) that is perpendicular to axis 16 and intersects object 18. Direction 22 is aimed radially away from the origin. The 90° redirection from initial direction 14 to intermediate directing 22 is done in two stages of, for example, 45° each by two beam-bending magnetic fields in regions 24, 26. A set of magnetic quadrupole lenses in region 28 in combination with magnetic fields 24, 26 forms an achromat as defined in *Focusing of Charged Particles,* Vol. II, Ed: A. Septier, Academic Press NY 1967, Chapt. 4.2, "Deflecting Magnets", p. 228, FIG. 12.

Next the beam is redirected for example 270° within the treatment plane to a final direction 30 that is radially toward the origin. The 270° redirection is accomplished (within a single quadrant of a circle) in two stages of 135° each by an achromat consisting of two magnetic fields in regions 32, 34 and a set of quadrupole lenses between them, in region 36.

The beam then passes through a scattering mechanism in region 38. At point 40 the scattered beam reaches the exit of an evacuated pipe (not shown) through which the beam has been conducted along the entire path beginning at fixed source 10 and ending at point 40. From point 40 to object 18 the beam drifts in air.

In order to be able to direct the beam toward object 18 along a variety of different directions within the treatment plane all of the movable elements (including evacuated pipe, magnets, lenses, and scatters) along the path beginning at point 42 and ending at point 40 are mounted on a gantry that is rotatable about axis 16 (as suggested by arrows 46). For example, by rotating the gantry counterclockwise (arrow 47) a new final direction 48 for the beam path can be achieved. A bearing at location 42 (along with other elements to be described below) permits the gantry to rotate while the beam source remains fixed.

Figure 2:
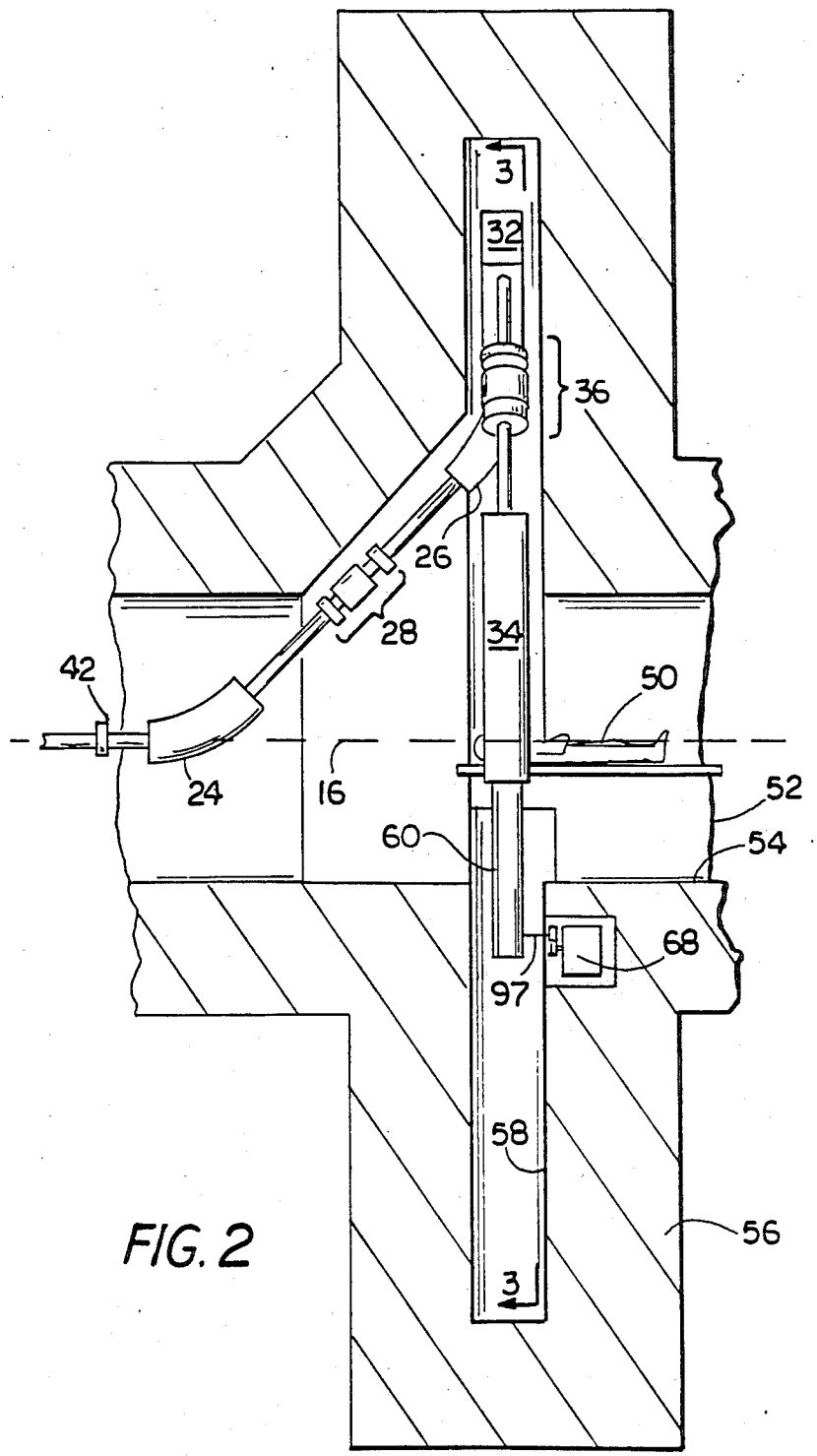
FIG. 2 is a side view of portions of a gantry with associated shielding shown in section.

Referring to FIG. 2, a patient 50 to be treated lies on a platform 52 positioned to be struck by the beam delivered in direction 30. Platform 52 is supported on a floor 54 formed on the surface of concrete shielding 56. To accommodate the rotation of magnets 24, 26, 32, 34, leanses 28, 36, and scattering mechanism 38, shielding 56 is provided with a slot-shaped cavity 58. Because much of the beam redirection is effected by magnets that are in the treatment plane, cavity 58 may be made very narrow (in the direction of axis 16), e.g., 24" wide. As a result, the building required to house the gantry may be smaller and less costly, and require less concrete then for a U-shaped gantry. The pieces of the gantry are supported on a rigid support ring 60 (e.g., 16 feet in diameter). The gantry is held in a precise radial position and the weight of the gantry is supported by a pair of a wheel assemblies located at positions 71, 73. (FIG. 3)

Referring to FIGS. 5, 6, each wheel assembly includes a pair of aircraft-type ball-bearing supported wheels 75 connected by bars 77. A rod 79 attached at the midpoint of bar 77 has its other end mounted in shielding concrete 56. In cross-section ring 60 is an I-beam. Each counterweight 81 is attached to ring 60 by a bracket 83 and wheels 75 engage an inner wall surface of bracket 83 as shown, thus bearing the weight of, and maintaining the raial position of, ring 60.

Figure 3:
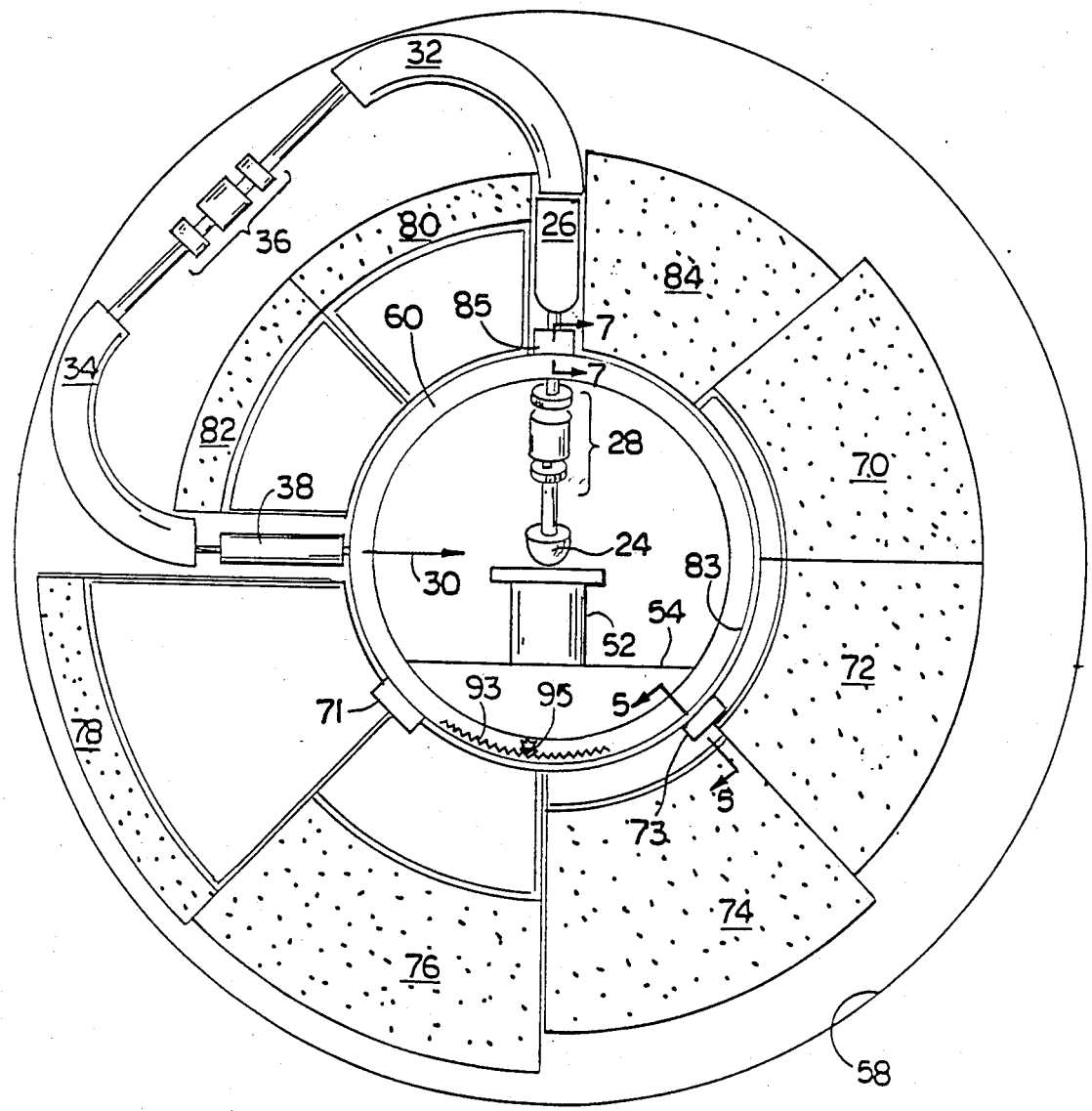
FIG. 3 is a rear view, at 3—3 of FIG. 2, of portions of the gantry.

Referring to FIG. 7, ring 60 is kept in a precise axial position by three roller assemblies 87 located at positions 71, 73, 85 (FIG. 3). Each assembly 87 includes two ball-bearing supported wheels 89 which straddle a rim 91 on ring 60. Wheels 89 contact opposite faces of rim 91 to maintain the axial position of ring 60.

In order to drive the gantry rotationally to any desired position, the inner face of rim 91 has gear teeth 93 that are engaged by a drive gear 95 (FIG. 3). Referring again to FIG. 2, the drive wheel shaft 95 (FIG. 2) is driven by an electric drive motor 68.

Referring to FIG. 3, in order to provide counterbalancing for the magnets, lenses, and scattering mechanism of the gantry, eight large concrete counterweights 70, 72, 74, 78, 80, 82, 84 are arranged about axis 16. The counterweights also effectively serve as shielding for scattered particles. Two of the heaviest counterweights 70, 72 are placed opposite scatterer 38 for maximum shielding. Two equally heavy counterweights 74, 76 cooperate with counterweights 70, 72 in offsetting the weight of the lenses, magnets, and scatterers. Counterweights 78, 80, 82, 84 serve to balance the entire system. The counterweights are attached to ring 60 by brackets 83. Note that the counterweights and brackets 83 are not shown in FIG. 2.

Referring to FIG. 4, the configuration of the gantry enables the gantry elements to be moved (as indicated by arrow 90) from a first angular position 92 in which direction 30 is vertically down, to a second position 94 in which direction 30' is vertically up, without requiring floor 54 to be punctured to accommodate the motion of magnets 24, 26 and lens 28. That is possible because when the segment of the beam path between magents 24, 26 is horizontal, direction 30 is vertical. By providing slots in the floor, of course, it would be possible to achieve almost 360° of rotation.

In one possible configuration the system would have the following parameters.

| | |
|---|---|
| beam energy | 200–250 Mev. |
| counterweights 70, 72, 74, 76 | 10 tons each |
| counterweights 80, 82 | 2 tons each |
| counterweights 78 | 3 tons |
| counterweights 74 | 6 tons |
| lens 36 | 1.5 tons |
| magnets 32, 34 | 7.5 tons each |
| radius of gantry | 18 feet |

Other embodiments are within the following claims. For example, it may be useful to redirect the beam by more than 270° in the treatment plane by relocating and reconfiguring magnets 32, 34.

I claim:

1. Apparatus for redirecting a particle beam from an initial direction lying along an initial axis, to a final direction lying in a plane which intersects said axis, said final direction being other than radially away from said axis, said apparatus comprising:
   a first redirection structure for redirecting said beam from said initial direction to an intermediate direction lying in said plane, and
   a second redirection structure for redirecting said beam within said plane from said intermediate direction to said final direction.

2. The apparatus of claim 1 wherein said second redirection structure is mounted for rotation about said axis.

3. The apparatus of claim 1 wherein said second redirection structure lies generally in a plane.

4. The apparatus of claim 1 further comprising counterweights arranged about said axis for counterbalancing said second redirection structure.

5. The apparatus of claim 4 wherein said counterweights are configured to provide radiation shielding.

6. The apparatus of claim 5 wherein there is a set of distinct said counterweights arranged at different positions about said axis, different said counterweights having different weights.

7. The apparatus of claim 1 wherein said first and second redirection structures comprise means for redirecting a proton beam.

8. The apparatus of claim 1 wherein said plane intersects a region of interest in a body and in said final direction said beam is aimed at said region of interest.

9. The apparatus of claim 1 wherein said plane is perpendicular to said axis.

10. The apparatus of claim 1 wherein said final direction is radially toward said axis.

11. The apparatus of claim 1 wherein said first redirection structure redirects said beam through an aggregate angle of 90°.

12. The apparatus of claim 1 wherein said first redirection structure comprises two spaced apart substructures for effecting respectively two stages of the redirection of said beam.

13. The apparatus of claim 12 wherein said two spaced apart substructures each effect 45° of redirection of said beam.

14. The apparatus of claim 1 wherein said second redirection structure redirects said beam along a pth that lies substantially within a single quadrant of said plane.

15. The apparatus of claim 1 wherein said second redirection structure redirects said beam through an aggregate angle of approximately 270°.

16. The apparatus of claim 15 wherein said second redirection structure comprises two spaced apart substructures effecting respectively two stages of the redirection of said beam.

17. The apparatus of claim 16 wherein said two spaced apart substructures each effect 135° of redirection of said beam.

18. The apparatus of claim 1 wherein said redirection structures comprise magnets.

19. The apparatus of claim 1 wherein said redirection structures comprise achromats.

20. The apparatus of claim 1 further comprising means for shifting said final direction through a range of orientations.

21. The apparatus of claim 1 wherein said first redirection structure comprises a bearing permitting rotation of said first redirection structure about said axis during rotation of said second redirection structure about said axis.

22. The apparatus of claim 21 wherein said first redirection structure lies in a plane perpendicular to said plane in which said final direction lies.

23. The apparatus of claim 22 wherein said second redirection structure is configured so that while said final direction moves through a 180° range of positions from vertically up to vertically down, said first redirection structure moves through a range of positions all at or above a horizontal plane.

24. A method for redirecting a particle beam from an initial direction lying along an initial axis, to a final direction lying in a plane which intersects said axis, said final direction being other than radially away from said axis, said method comprising redirecting said beam from said initial direction to an intermediate direction lying in said plane, and redirecting said beam within said plane from said intermediate direction to said final direction.

25. A gantry for redirecting a particle beam from a fixed source to any one of a range of paths each of which is aimed at an object of interest, said paths all lying in a common plane intersecting said object, said gantry comprising:
first means for bending said beam to lie in said plane in a direction not aimed at said object,
second means for bending said beam within said plane to cause said beam to be aimed at said object, and
means for rotating said second bending means about said object to cause said beam aimed at said object to traverse said range of paths.

* * * * *